(12) United States Patent
Chen et al.

(10) Patent No.: US 9,416,072 B1
(45) Date of Patent: *Aug. 16, 2016

(54) SELECTIVE HYDROGENATION OF STYRENE TO ETHYLBENZENE

(71) Applicant: ExxonMobil Chemical Patents Inc., Baytown, TX (US)

(72) Inventors: Tan-Jen Chen, Kingwood, TX (US); John D. Ou, Houston, TX (US); Jeevan S. Abichandani, Houston, TX (US); Glenn A. Heeter, The Woodlands, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/143,887

(22) Filed: May 2, 2016

Related U.S. Application Data

(62) Division of application No. 14/165,255, filed on Jan. 27, 2014, now Pat. No. 9,353,024.

(60) Provisional application No. 61/761,402, filed on Feb. 6, 2013.

(51) Int. Cl.
| | |
|---|---|
| *C07C 2/66* | (2006.01) |
| *C07C 7/00* | (2006.01) |
| *C07C 5/03* | (2006.01) |
| *C07C 5/10* | (2006.01) |
| *C07C 5/05* | (2006.01) |
| *C07C 7/163* | (2006.01) |
| *C07C 2/86* | (2006.01) |

(52) U.S. Cl.
CPC .............. *C07C 7/163* (2013.01); *C07C 2/864* (2013.01); *C07C 2/865* (2013.01)

(58) Field of Classification Search
CPC .............. C07C 2/66; C07C 7/00; C07C 5/03; C07C 5/10; C07C 5/05
USPC .......................... 585/805, 467, 266, 267, 269
See application file for complete search history.

(56) References Cited

U.S. PATENT DOCUMENTS

| | | | |
|---|---|---|---|
| 3,684,665 | A | 8/1972 | Hisao et al. |
| 4,002,698 | A | 1/1977 | Kaeding |
| 4,356,338 | A | 10/1982 | Young |
| 4,423,266 | A | 12/1983 | Young |
| 5,675,047 | A | 10/1997 | Beck et al. |
| 5,804,690 | A | 9/1998 | Chang et al. |
| 5,939,597 | A | 8/1999 | Dessau et al. |
| 6,028,238 | A | 2/2000 | Beck et al. |
| 6,046,372 | A | 4/2000 | Brown et al. |
| 6,048,816 | A | 4/2000 | Brown et al. |
| 6,156,949 | A | 12/2000 | Brown et al. |
| 6,423,879 | B1 | 7/2002 | Brown et al. |
| 6,504,072 | B1 | 1/2003 | Brown et al. |
| 6,506,954 | B1 | 1/2003 | Brown et al. |
| 6,538,167 | B1 | 3/2003 | Brown et al. |
| 6,642,426 | B1 | 11/2003 | Johnson et al. |
| 7,592,499 | B2 | 9/2009 | Wolff et al. |
| 8,481,443 | B2 | 7/2013 | Levin et al. |
| 2011/0160503 | A1 | 6/2011 | Fischer et al. |
| 2012/0149958 | A1 | 6/2012 | Ellrich et al. |
| 2013/0165724 | A1 | 6/2013 | Han et al. |

OTHER PUBLICATIONS

U.S. Appl. No. 61/496,262, filed Jun. 13, 2011, Bender et al.
U.S. Appl. No. 61/604,926, filed Feb. 29, 2012, Ross et al.
U.S. Appl. No. 61/681,486, filed Aug. 9, 2012, Heeter et al.
U.S. Appl. No. 61/711,341, filed Oct. 9, 2012, Tinger et al.
U.S. Appl. No. 61/761,402, filed Feb. 6, 2013, Chen et al.
Badano et al., "*Low metal loading catalysts used for the selective hydrogenation of styrene*", Quimica Nova, vol. 33, No. 1, pp. 48-51 (2010).

*Primary Examiner* — Thuan D Dang

(57) ABSTRACT

A feedstream comprising paraxylene and styrene is contacted, in the presence of hydrogen, with a catalyst comprising at least one metal, selected from one or more metals selected from Groups 8-10.

9 Claims, No Drawings

SELECTIVE HYDROGENATION OF STYRENE TO ETHYLBENZENE

PRIORITY

This application is a divisional of and claims priority to U.S. patent application Ser. No. 14/165,255, filed Jan. 27, 2014, and U.S. Provisional Application No. 61/761,402, filed Feb. 6, 2013, the disclosures of which are incorporated by reference in their entirety.

FIELD OF THE INVENTION

The invention relates to the selective hydrogenation of styrene to ethylbenzene and more particularly to the removal of small quantities of styrene present in the product stream of a method of making paraxylene selectively by the alkylation of aromatic species with an alkylating agent over a solid catalyst.

BACKGROUND OF THE INVENTION

It is well-known to manufacture xylenes by the alkylation of toluene and/or benzene with methanol, and in particular to selectively make paraxylene (PX) product using zeolite catalyst. See, for instance, U.S. Pat. Nos. 4,002,698; 4,356,338; 4,423,266; 5,675,047; 5,804,690; 5,939,597; 6,028,238; 6,046,372; 6,048,816; 6,156,949; 6,423,879; 6,504,072; 6,506,954; 6,538,167; and 6,642,426. See also more recently U.S. application Ser. No. 13/557,605, and references cited therein. Paraxylene selectivity is highly sought after because of the economic importance of paraxylene relative to meta- and orthoxylene. Although each of the xylene isomers have important and well-known end uses, paraxylene is currently the most economically valuable, serving as an intermediate in such important and diverse end uses as bottle plastic and polyester fibers.

One of the problems with xylenes streams produced by alkylating aromatic species such as benzene and/or toluene with alkylating agents such as methanol and/or dimethyl ether over solid catalysts, such as in the aforementioned processes, is the product stream may contain styrene impurities. This has recently been observed and set forth in Provisional Patent Applications 61/711,341 and 61/681,486. Styrene impurities can cause operability problems for downstream process, for example paraxylene recovery by adsorptive separation processes, e.g., Parex™ Process or Eluxyl™ Process, as well as other processes used to take paraxylene to end products, such as in processes used to make purified terephthalic acid/anhydride and subsequent steps to making fibers or bottle plastic therefrom.

One method of removing styrene is to convert said species to ethylbenzene by selective hydrogenation. Several characteristics of purifying xylenes containing styrene impurities make selective hydrogenation of styrene challenging. It is highly desirable to minimize the ring saturation reactions since separation of dimethylcyclohexane, ethylcyclohexane, and/or other saturated C8 hydrocarbons from xylenes is difficult. Another potential challenge is that the desired product, paraxylene, is present at higher-than-equilibrium concentration. The catalyst used to hydrogenate styrene must therefore show minimal xylenes isomerization activity.

It is known to hydrogenate certain aromatic species in paraxylene enriched streams. See, for instance, U.S. application Ser. Nos. 61/604,926, 61/496,262, 13/303,855, and 13/449,758.

The present inventors have surprisingly discovered a method of selectively hydrogenating styrene impurities present in a xylenes stream nearly stoichiometrically using a catalyst comprising at least one metal selected Groups 8-10 of the Periodic Table, optionally further comprising promoters and/or supports.

SUMMARY OF THE INVENTION

The invention is directed to a method of hydrogenating styrene impurities present in a xylenes stream using a catalyst comprising M, wherein M is selected from Group 8-10 metals, preferably Pd, Co, Ni, Ru, and mixtures thereof.

In embodiments, promoters such as Ag, Au, In, K and other alkali metals, Ca and other alkaline earth metals, and mixtures thereof, can be present.

In embodiments, a support such as $Al_2O_3$, carbon, $SiO_2$, $TiO_2$, and mixtures thereof, may be present.

It is an object of the invention to eliminate styrene from paraxylene-containing feedstreams prior to processes that would have operability problems with even small quantities of styrene, e.g., catalytic processes, absorption processes, and the like, that are sensitive to the presence of vinyl moiety, while having little or no effect, e.g., ring saturation and/or isomerization, on paraxylene itself.

These and other objects, features, and advantages will become apparent as reference is made to the following detailed description, preferred embodiments, examples, and appended claims.

DETAILED DESCRIPTION

According to the invention, a feedstream comprising paraxylene and styrene is contacted in the presence of hydrogen with a catalyst comprising one or more metals selected from Groups 8-10 of the Periodic Table, preferably Pd, Co, Ni, Ru, and mixtures thereof.

In embodiments, promoters such as Ag, Au, In, K and other alkali metals (Group 1 metals), Ca and other alkaline earth metals (Group 2 metals), and mixtures thereof, can be present.

In embodiments, a support such as carbon, alumina ($Al_2O_3$), silica ($SiO_2$), titania ($TiO_2$) and mixtures thereof, may be present.

In preferred embodiments the amount of paraxylene in the feedstream from the alkylation reaction is enriched from equilibrium concentration, i.e., greater than about 24 wt %, and in preferred embodiments is in the amount of from 70 wt % to 98 wt %, or 75 wt % to 92 wt %, or 80 wt % to 89 wt %.

In embodiments the amount of styrene in the feedsteam from the alkylation reactor is in the range of from 0.01 wt % to 2.00 wt %, or 0.05 wt % to 1.00 wt %, or 0.08 wt % to 0.50 wt %.

In preferred embodiments, less than 0.2 wt % of the paraxylene is isomerized in the step of contacting one or more metals selected from Groups 8-10.

In preferred embodiments, there is no detectable ethylcyclohexane or dimethylcyclohexane in the product (based on gas chromatographic analysis) in the step of contacting one or more metals selected from Groups 8-10.

The preferred catalyst for the alkylation reaction comprises ZSM-5, which has been severely steamed at a temperature of at least 950° C. in the presence of at least one oxide modifier, preferably including phosphorus, to control reduction of the micropore volume of the material during the steaming step. See U.S. Pat. Nos. 6,423,879 and 6,504,072. The preferred alkylating agent is methanol or dimethyl ether and the preferred aromatic species alkylated is benzene and/or toluene.

The invention will be better understood by reference to the following example, which will be understood by those of ordinary skill in the art to be representative and not limiting thereof.

To illustrate the effectiveness of Pd catalysts in hydrogenation of styrene by-product found in xylene product stream from an alkylation reactor such as a fluid bed reactor having staged baffles, such as described in U.S. application Ser. No. 13/557,605, and such as according to the process described in U.S. Provisional Application 61/681,486, a run was made with Axens™ LD269 catalyst and a feed consisted of 0.10% styrene, 0.62% ethylbenzene, 78.72% para-xylene, 14.66% meta-xylene, and 5.58% ortho-xylene. Axens™ LD269 is a commercially available catalyst used for butene hydrogenation. It is a $Pd/Al_2O_3$ catalyst based on the information available in the public domain. The test was carried out in a down flow micro-lab unit at 100° C., 165 psig, 5 $hr^{-1}$ WHSV, and 1/1 $H_2$/HC molar ratio. Key results from the test are summarized in the table below.

TABLE 1

HIGH CONVERSION AND HIGH SELECTIVITY
ACHIEVED IN HYDROGENATION OF STYRENE
(100° C., 165 psig, 1/1 $H_2$/HC molar ratio, 5 $hr^{-1}$ WHSV)

| Components, wt % | Feed | Product |
|---|---|---|
| Toluene | 0.13 | 0.12 |
| Ethylbenzene | 0.62 | 0.72 |
| Para-Xylene | 78.72 | 78.63 |
| Meta-Xylene | 14.66 | 14.71 |
| Ortho-Xylene | 5.58 | 5.60 |
| Styrene | 0.10 | 0.00 |
| Phenol | 0.0012 | 0.0011 |
| Styrene Conversion | NA | 100 |
| Styrene Selectivity to EB | NA | 100 |

As can be seen from the table, Axens™ LD 269 catalyst is very effective in hydrogenating styrene present in the mixed xylene feed to ethylbenzene. No measurable styrene was found in the product by gas chromatography, equipped with wax column. The detection limit of the GC is 5 ppm. This suggests that conversion was nearly 100% if not 100% at 100° C., 165 psig, and 5 $hr^{-1}$ WHSV. Selectivity was also nearly 100% if not 100% since all the styrene which was converted can be accounted by for the increase in ethylbenzene. No ethylcyclohexane or dimethylcyclohexane was detected in the product. The detection limit of the GC for measuring ethylbenzene, ethylcyclohexane and dimethylcyclohexane was also 5 ppm.

In addition to being highly active and selective in hydrogenation of styrene to ethylbenzene, $Pd/Al_2O_3$ catalysts such as Axens™ LD269 were also found to have minimal activity in isomerization of para-xylene to ortho-xylene or para-xylene. As can be seen from the table, only ~0.1 wt % para-xylene was isomerized to either ortho-xylene or meta-xylene (based on the total amount of para-xylene). The relatively complete conversion of styrene and lack of typical isomerization products by contact of a mixed xylene feed was highly surprising.

The invention has been described above with specificity however it will be understood by one of ordinary skill in the art in possession of the present disclosure that the invention may be practiced other than as specifically set forth herein, such as in fixed bed reactors, moving bed reactors, and the like.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. Trade names used herein are indicated by a ™ symbol or ® symbol, indicating that the names may be protected by certain trademark rights, e.g., they may be registered trademarks in various jurisdictions. When numerical lower limits and numerical upper limits are listed herein, ranges from any lower limit to any upper limit are contemplated.

What is claimed is:

1. A process comprising:
   (i) contacting an aromatic hydrocarbon feedstream comprising benzene and/or toluene with methanol and/or dimethyl ether in the presence of a phosphorus-modified ZSM-5 alkylation catalyst, which has been steamed at a temperature of at least 950° C., to obtain a first product stream comprising greater than about 24 wt % para-xylene and styrene; and
   (ii) contacting said first product stream comprising greater than about 24 wt % para-xylene and styrene with a hydrogenation catalyst comprising at least one metal selected from Groups 8-10 of the Periodic Table, in the presence of hydrogen, to obtain a second product stream comprising a reduced amount of styrene when compared with said first product stream, wherein less than 0.2 wt % of paraxylene is isomerized by contact with the hydrogenation catalyst.

2. The process of claim 1, wherein said second product stream is further characterized as having no detectable levels of styrene, ethylcyclohexane and dimethylcyclohexane, as measured by gas chromatography.

3. The process of claim 1, wherein said hydrogenation catalyst further comprises a support selected from $Al_2O_3$, carbon, $SiO_2$, $TiO_2$, and mixtures thereof.

4. The process of claim 1, wherein said metal is selected from Pd, Co, Ni, Ru, and mixtures thereof.

5. The process of claim 1, wherein said hydrogenation catalyst further comprises at least one metal or metal compound selected from Ag, Au, In, alkali metals, and alkaline earth metals.

6. The process of claim 1, wherein said second product stream contains an increased amount of ethylbenzene relative to said feedstream.

7. The process of claim 6, wherein said increased amount of ethylbenzene is equal to the amount of styrene in said first product stream as measured by gas chromatography.

8. The process of claim 1, wherein the amount of paraxylene in the first product stream comprises at least 70 wt % based on the total xylene concentration.

9. The process of claim 1, wherein the amount of styrene in the first product stream comprises about 0.01 wt % to 2.00 wt %.

* * * * *